United States Patent
Jeong et al.

(10) Patent No.: US 10,720,665 B2
(45) Date of Patent: Jul. 21, 2020

(54) LITHIUM SECONDARY BATTERY INCLUDING A PERFLUORO NITRILE COMPOUND

(71) Applicant: SOULBRAIN CO., LTD., Gyeonggi-do (KR)

(72) Inventors: Myung Hoon Jeong, Gyeonggi-do (KR); Jong Hyun Lee, Gyeonggi-do (KR); Seung Hoon Jung, Gyeonggi-do (KR)

(73) Assignee: SOULBRAIN CO., LTD., Gyeonggi-do (KR)

(*) Notice: Subject to any disclaimer, the term of this patent is extended or adjusted under 35 U.S.C. 154(b) by 188 days.

(21) Appl. No.: 15/737,396

(22) PCT Filed: Jun. 22, 2016

(86) PCT No.: PCT/KR2016/006587
§ 371 (c)(1),
(2) Date: Dec. 18, 2017

(87) PCT Pub. No.: WO2016/208946
PCT Pub. Date: Dec. 29, 2016

(65) Prior Publication Data
US 2018/0183100 A1    Jun. 28, 2018

(30) Foreign Application Priority Data

Jun. 22, 2015 (KR) .................. 10-2015-0088579
Jun. 22, 2016 (KR) .................. 10-2016-0077676

(51) Int. Cl.
*H01M 10/05* (2010.01)
*H01M 10/0567* (2010.01)
(Continued)

(52) U.S. Cl.
CPC ....... *H01M 10/0567* (2013.01); *C07C 255/10* (2013.01); *H01M 10/052* (2013.01);
(Continued)

(58) Field of Classification Search
None
See application file for complete search history.

(56) References Cited

U.S. PATENT DOCUMENTS

2003/0157412 A1    8/2003    Yamaguchi et al.
2005/0084765 A1    4/2005    Lee et al.
(Continued)

FOREIGN PATENT DOCUMENTS

CN    102412418 B    3/2014
EP    2302725 A1    3/2011
(Continued)

OTHER PUBLICATIONS

European Patent Office, Extended European Search Report of corresponding EP Patent Application No. 16814659.5, dated Mar. 26, 2018.

*Primary Examiner* — Ula C Ruddock
*Assistant Examiner* — Tony S Chuo
(74) *Attorney, Agent, or Firm* — IP Legal Services, LLC

(57) ABSTRACT

The present invention relates to an electrolyte for a lithium secondary battery, containing, as an electrolyte additive, at least one compound selected from the group consisting of compounds represented by chemical formulas 1 to 4 below, and can provide a lithium secondary battery which has improved anodic film forming characteristics and battery resistance characteristics at high voltages.

12 Claims, 2 Drawing Sheets

(51) Int. Cl.
*H01M 10/0525* (2010.01)
*H01M 10/0569* (2010.01)
*C07C 255/10* (2006.01)
*H01M 10/052* (2010.01)
*H01M 4/62* (2006.01)
*H01M 4/525* (2010.01)
*H01M 4/587* (2010.01)

(52) U.S. Cl.
CPC ... *H01M 10/0525* (2013.01); *H01M 10/0569* (2013.01); *H01M 4/525* (2013.01); *H01M 4/587* (2013.01); *H01M 4/623* (2013.01); *H01M 2300/004* (2013.01); *H01M 2300/0025* (2013.01)

(56) References Cited

U.S. PATENT DOCUMENTS

| | | |
|---|---|---|
| 2005/0208371 A1 | 9/2005 | Kim et al. |
| 2008/0248397 A1 | 10/2008 | Jung et al. |
| 2009/0047582 A1 | 2/2009 | Kim et al. |
| 2010/0104949 A1 | 4/2010 | Yamaguchi et al. |
| 2011/0050178 A1 | 3/2011 | Kim et al. |
| 2011/0052980 A1 | 3/2011 | Sakata et al. |
| 2013/0091702 A1 | 4/2013 | Kim et al. |
| 2013/0157119 A1 | 6/2013 | Shimura et al. |
| 2015/0093602 A1 | 4/2015 | Jung et al. |
| 2015/0104717 A1 | 4/2015 | Kim et al. |

FOREIGN PATENT DOCUMENTS

| | | |
|---|---|---|
| JP | 2000-124077 A | 4/2000 |
| JP | 2002-302649 A | 10/2002 |
| JP | 2003-007336 A | 1/2003 |
| JP | 2003-197254 A | 7/2003 |
| JP | 2007-510270 A | 4/2007 |
| JP | 2010-238385 A | 10/2010 |
| JP | 2013-201150 A | 10/2013 |
| JP | 2013-232326 A | 11/2013 |
| KR | 10-2005-0020067 A | 3/2005 |
| KR | 10-2005-0075297 A | 7/2005 |
| KR | 10-0814827 B1 | 3/2008 |
| KR | 10-0873577 B1 | 12/2008 |
| WO | 2009/136589 A1 | 11/2009 |
| WO | 2012/029388 A1 | 3/2012 |

LITHIUM SECONDARY BATTERY INCLUDING A PERFLUORO NITRILE COMPOUND

CROSS REFERENCE TO RELATED APPLICATIONS

This application is a National Stage Patent Application of PCT International Patent Application No. PCT/KR2016/006587 (filed on Jun. 22, 2016) under 35 U.S.C. § 371, which claims priority to Korean Patent Application Nos. 10-2015-0088579 (filed on Jun. 22, 2015) and 10-2016-0077676 (filed on Jun. 22, 2016), the teachings of which are incorporated herein in their entireties by reference.

TECHNICAL FIELD

The present disclosure relates to an electrolyte capable of improving battery characteristics of a lithium secondary battery, particularly, capable of improving a cathode film forming characteristic and a battery resistance characteristic at a high voltage, and a lithium secondary battery including the same.

BACKGROUND ART

Application of a lithium secondary battery is rapidly expanded not only as portable power sources for mobile phones, notebook computers, digital cameras, and camcorders, etc., but also as medium and large power sources for power tools, electric bicycles, hybrid electric vehicles (HEV), plug-in hybrid electric vehicles (PHEV), etc. As these application fields are expanded and the demand is increased, an external shape and a size of the battery are variously changed, and performance and stability are required to be higher than those required in conventional small batteries. In order to meet such a demand, performance of the battery should be stably implemented under a condition that a large current flows.

The lithium secondary battery is produced by using materials capable of inserting and removing lithium ions as an anode and a cathode, installing a porous separator between the two electrodes, and injecting a liquid electrolyte. Electricity is generated or consumed by an oxidation-reduction reaction according to the insertion and removal of the lithium ions in the anode and the cathode.

Various reviews on non-aqueous solvents or additives have been studied as components provided in an electrolyte in order to improve battery characteristics such as output characteristics, cycle characteristics, and storage characteristics, etc., of the lithium ion battery. Further, even when a specific compound is added to the electrolyte as an additive in order to improve the battery performance, performance of some items of most battery performance may be expected to be improved, but the performance of other items is rather reduced.

DISCLOSURE

Technical Problem

An object of the present disclosure is to provide an electrolyte capable of improving battery characteristics of a lithium secondary battery, particularly, capable of improving a cathode film forming characteristic and a battery resistance characteristic at a high voltage.

Another object of the present disclosure is to provide a lithium secondary battery including the electrolyte.

Technical Solution

In one general aspect, an electrolyte for a lithium secondary battery includes a perfluoro nitrile compound as an electrolyte additive.

The perfluoro nitrile compound may be any one selected from the group consisting of a perfluoro mononitrile compound, a perfluoro dinitrile compound, a perfluoro trinitrile compound, a perfluoro tetranitrile compound, and a combination thereof.

The perfluoro nitrile compound may be represented by Chemical Formulas 1 to 4 below:

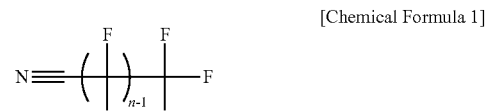

[Chemical Formula 1]

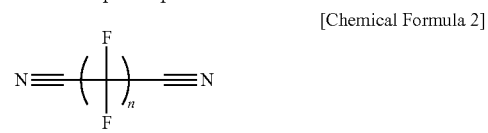

[Chemical Formula 2]

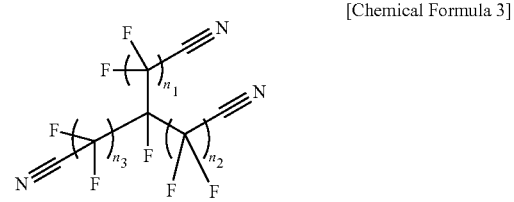

[Chemical Formula 3]

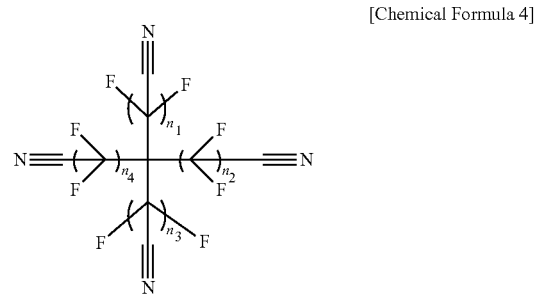

[Chemical Formula 4]

wherein n is 1 to 15.

The perfluoro nitrile compound may be perfluorohexane-1,6-dinitrile.

The electrolyte for a lithium secondary battery may further include hexane-1,6-dinitrile.

The hexane-1,6-dinitrile may have a content of 1 to 80 parts by weight based on 100 parts by weight of the perfluorohexane-1,6-dinitrile.

The electrolyte for a lithium secondary battery may further include an organic solvent and a lithium salt.

In another general aspect, a lithium secondary battery includes: a cathode including a cathode active material, an anode disposed opposite to the cathode and including an anode active material, and an electrolyte interposed between the cathode and the anode, wherein the electrolyte includes a perfluoro nitrile compound as an electrolyte additive.

The electrolyte additive may have a content of 0.1 to 10 wt % based on the total weight of the electrolyte.

The perfluoro nitrile compound may be perfluorohexane-1,6-dinitrile.

The electrolyte for a lithium secondary battery may further include hexane-1,6-dinitrile.

The hexane-1,6-dinitrile may have a content of 1 to 80 parts by weight based on 100 parts by weight of the perfluorohexane-1,6-dinitrile.

Advantageous Effects

The electrolyte for a lithium secondary battery according to the present disclosure may improve the battery characteristics of the lithium secondary battery, particularly, the cathode film forming characteristic and the battery resistance characteristic at the high voltage.

BEST MODE

Figure 1:
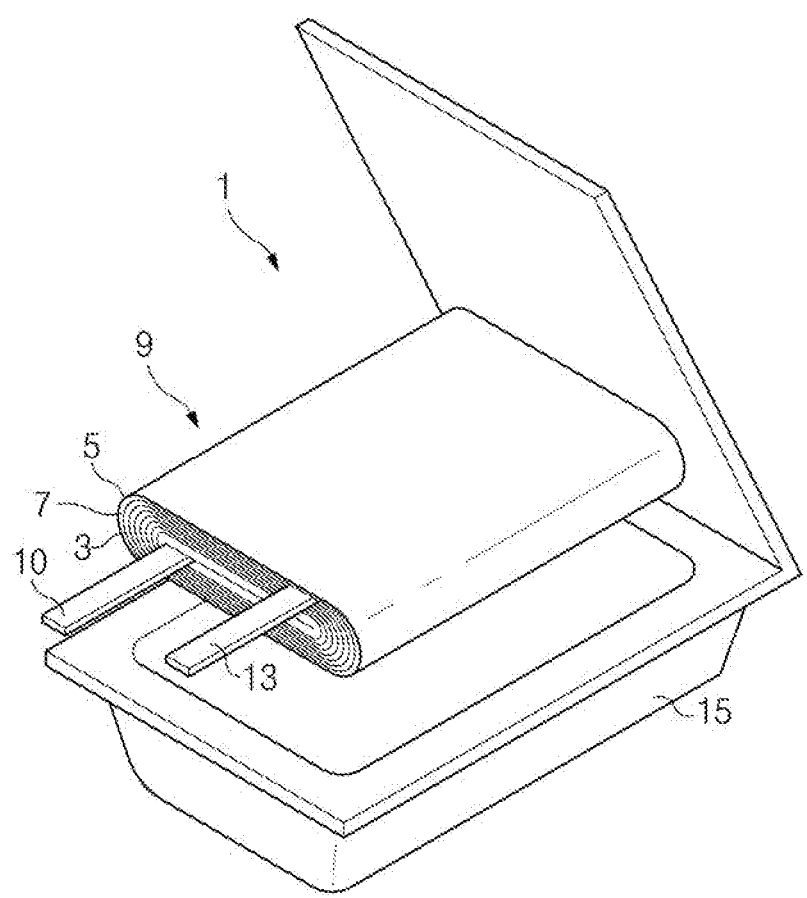
FIG. 1 is a partial perspective view of a lithium secondary battery according to an exemplary embodiment of the present disclosure.

Hereinabove, although the present disclosure can be modified variously and have several embodiments, the exemplary embodiments are illustrated and will be described in more detail in the detailed description. However, the present disclosure is not limited to the specific embodiments and should be construed as including all the changes, equivalents, and substitutions included in the spirit and scope of the present disclosure.

The terms used in the specification are used to describe only specific embodiments and are not intended to limit the present disclosure. As used herein, the singular forms are intended to include the plural forms as well, unless the context clearly indicates otherwise. It will be further understood that the term "comprises" or "have" used in this specification, specify the presence of stated features, steps, operations, components, parts, or a combination thereof, but do not preclude the possibility of the presence or addition of one or more other features, numerals, steps, operations, components, parts, or a combination thereof.

Further, term "a combination thereof" used herein means that two or more substituents are bonded to each other through a single bond or a linking group, or two or more substituents are condensed and connected unless otherwise specified.

The electrolyte according to an exemplary embodiment of the present disclosure includes a perfluoro nitrile compound as an electrolyte additive. Here, the perfluoro nitrile compound means a hydrocarbon compound including one or more nitrile groups, wherein all hydrogen atoms are substituted with fluorine. Further, the hydrocarbon compound means a hydrocarbon compound having 1 to 15 carbon atoms consisting of carbon and hydrogen, and includes an aliphatic chain type or branched hydrocarbon group and an alicyclic hydrocarbon group. Specific examples include propane, butane, pentane, hexane, heptane, octane, cyclohexane, benzene, toluene, xylene, biphenyl, and naphthalene, etc.

The perfluoro nitrile compound may be any one selected from the group consisting of a perfluoro mononitrile compound, a perfluoro dinitrile compound, a perfluoro trinitrile compound, a perfluoro tetranitrile compound, and a combination thereof, according to the number of nitrile groups.

Specifically, the perfluoro mononitrile compound may be represented by Chemical Formula 1 below:

[Chemical Formula 1]

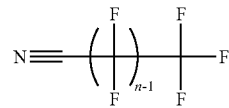

wherein n is 1 to 15.

More specifically, the perfluoro mononitrile compound may have a linear form or a branched form such as NC—$CF_3$, NC—$CF_2CF_3$, NC—$CFCF_3CF_3$, NC—$CF_2CF_2CF_3$, etc.

Further, the perfluoro dinitrile compound may be represented by Chemical Formula 2 below:

[Chemical Formula 2]

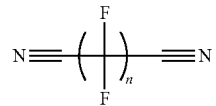

wherein n is 1 to 15.

More specifically, the perfluoro dinitrile compound may be any one selected from the group consisting of perfluoro dinitrile in a linear form, such as NC—$CF_2$—CN, NC—$CF_2CF_2$—CN, NC—$CF_2CF_2CF_2$—CN, NC—$CF_2CF_2CF_2CF_2$—CN, NC—$CF_2CF_2CF_2CF_2CF_2$—CN, NC—$CF_2CF_2CF_2CF_2CF_2CF_2$—CN, NC—$CF_2CF_2CF_2CF_2CF_2CF_2CF_2$—CN, etc., and perfluoro dinitrile in a branched form, such as [NC—$CF_2CF(CF_3)CF_2$—CN], NC—$CF_2CF_2CF_2CF(CN)$ $CF_3$, etc., and a combination thereof.

Further, the perfluoro trinitrile compound may be represented by Chemical Formula 3 below:

[Chemical Formula 3]

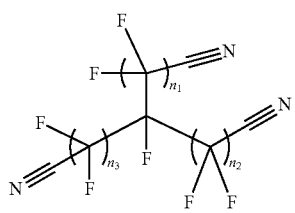

wherein $n_1$ to $n_3$ are each independently 1 to 15.

More specifically, the perfluoro trinitrile compound may have a branched form, such as CF—$(CF_2$—$CN)_2$ $(CF_2CF_2$—CN), CF— $(CF_2$—$CN)_2$ $(CF_2CF_2CF_2$—CN), CF— $(CF_2$—$CN)_2$ $(CF_2CF_2CF_2CF_2$—CN), CF— $(CF_2$—$CN)_2$ $(CF_2CF_2CF_2CF_2CF_2$—CN) or CF—$(CF_2$—CN) CF—$(CF_2$—$CN)_2$ $(CF_2CF_2$—CN), CF— $(CF_2$—CN) $(CF_2CF_2$—$CN)_2$, CF— $(CF_2$—CN) $(CF_2CF_2$—CN) $(CF_2CF_2CF_2$—CN), etc.

Further, the perfluoro tetranitrile compound may be represented by Chemical Formula 4 below:

[Chemical Formula 4]

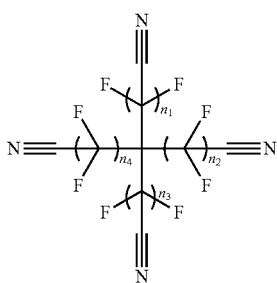

wherein $n_1$ to $n_4$ are each independently 1 to 15.

More specifically, the perfluoro trinitrile compound may have a branched form, such as C—(CF$_2$—CN)$_3$ (CF$_2$CF$_2$—CN), C—(CF$_2$—CN)$_3$ (CF$_2$CF$_2$CF$_2$—CN), (CF$_2$—CN)$_3$ (CF$_2$CF$_2$CF$_2$CF$_2$—CN), C—(CF$_2$—CN)$_3$ (CF$_2$CF$_2$CF$_2$CF$_2$CF$_2$—CN), C—(CF$_2$—CN)$_3$ (CF$_2$CF$_2$CF$_2$CF$_2$CF$_2$CF$_2$CF$_2$CF$_2$—CN) or C—(CF$_2$—CN)$_4$, C—(CF$_2$—CN)$_3$(CF$_2$CF$_2$—CN), CF—(CF$_2$—CN)$_2$ (CF$_2$CF$_2$—CN)$_2$, etc.

When charging is performed in the battery, delithiation occurs in the cathode, and thus the cathode becomes unbalanced and performance deterioration occurs. According to the related art, the balance is recovered by adding succino nitrile (SN) as a cathode film forming additive. However, under a high voltage, the delithiation severely occurs, thereby making it difficult to meet charge balance with the succino nitrile (SN). According to the present disclosure, the electrolyte for a lithium battery including at least one electrolyte additive selected from the group consisting of the compounds represented by Chemical Formulas 1 to 4 may be used to solve the above-described problem.

When a lithium battery is charged at a high voltage, a large amount of lithium ions are discharged from the cathode, and the thus the balance of charge numbers at the cathode collapses. In the compounds represented by Chemical Formulas 1 to 4, the nitrile group (—CN) helps to form a film on the cathode, and fluorine (F), which is rich in electrons, fills deficient electrons to balance the cathode.

In Chemical Formulas 1 to 4, in consideration of an improvement degree in the battery characteristic improving effect according to the use of the electrolyte additive, it may be more preferable to use an alkylene group having 1 to carbon atoms, and more preferably, an alkylene group having 4 to 10 carbon atoms.

Specifically, the perfluoro nitrile compound represented by Chemical Formula 1 may be perfluoro pentane nitrile, the perfluoro dinitrile compound represented by Chemical Formula 2 may be perfluorohexane-1,6-dinitrile, the perfluoro trinitrile compound represented by Chemical Formula 3 may be 3-(cyano difluoro methyl)-2,2,3,4,4-penta fluoro pentane dinitrile, the perfluoro tetranitrile compound represented by Chemical Formula 4 may be 3,3-bis(cyano difluoromethyl)-2,2,4,4-tetra fluoro pentane dinitrile.

In particular, the perfluorohexane-1,6-dinitrile may be used together with hexane-1,6-dinitrile. When the perfluorohexane-1,6-dinitrile and the hexane-1,6-dinitrile are used together, it is possible to further improve the battery characteristics of the lithium secondary battery, particularly, the high-voltage lifetime and storage characteristics, and to obtain a synergistic effect in which the recovery capacity and the swelling characteristic are further improved.

Here, the hexane-1,6-dinitrile may have a content of 1 to 80 parts by weight, specifically, 5 to 70 parts by weight, and more specifically, 8 to 50 parts by weight based on 100 parts by weight of the perfluorohexane-1,6-dinitrile. When the content of the hexane-1,6-dinitrile is less than 1 part by weight based on 100 parts by weight of the perfluorohexane-1,6-dinitrile, sufficient electrons are not able to be supplied to the cathode during discharging, and thus the synergistic effect may not be obtained, and when the content thereof is more than 80 parts by weight, a thick film may be formed on the cathode, resulting in a large resistance.

The electrolyte additive including the perfluoronitrile compound represented by Chemical Formulas 1 to 4 may have a content of 0.1 to 10 wt %, preferably 0.2 to 7 wt %, and more preferably, 0.5 to 5 wt % based on the total weight of the electrolyte.

When the content of the electrolyte additive is less than 0.1 wt %, sufficient electrons may not be supplied to the cathode at the time of discharging, and thus the effect may not be obtained, and when the content of the electrolyte additive is more than 10 wt %, a thick film may be formed on the cathode, resulting in a large resistance.

When the perfluoro nitrile compound is used as the electrolyte additive, the battery characteristics of the lithium secondary battery, particularly, the lifetime characteristic and low resistance characteristic may be improved.

The electrolyte may further include an organic solvent and a lithium salt in addition to the electrolyte additive.

The organic solvent may be used without specific limitation as long as it is able to act as a medium through which ions involved in an electrochemical reaction of the battery are able to move. Specifically, the organic solvent may be an ester solvent, an ether solvent, a ketone solvent, an aromatic hydrocarbon solvent, an alkoxyalkane solvent, a carbonate solvent, or the like, wherein these solvents may be used alone or in combination of two or more thereof.

Specific examples of the ester solvent may include methyl acetate, ethyl acetate, n-propyl acetate, dimethyl acetate, methyl propionate, ethyl propionate, γ-butyrolactone, decanolide, γ-valerolactone, mevalonolactone, γ-caprolactone, δ-valerolactone, ε-caprolactone, etc.

Specific examples of the ether-based solvent may include dibutyl ether, tetraglyme, 2-methyltetrahydrofuran, tetrahydrofuran, etc.

Specific examples of the ketone-based solvent may include cyclohexanone, etc. Specific examples of the aromatic hydrocarbon-based organic solvent may include benzene, fluorobenzene, chlorobenzene, iodobenzene, toluene, fluorotoluene, xylene, or the like. Examples of the alkoxyalkane solvent may include dimethoxy ethane, diethoxy ethane, etc.

Specific examples of the carbonate solvent may include dimethyl carbonate (DMC), diethyl carbonate (DEC), dipropyl carbonate (DPC), methyl propyl carbonate (MPC), ethyl propyl carbonate (EPC), methyl ethyl carbonate (MEC), ethyl methyl carbonate (EMC), ethylene carbonate (EC), propylene carbonate (PC), butylene carbonate (BC), fluoroethylene carbonate (FEC), or the like.

Among them, it is preferable to use the carbonate-based solvent as the organic solvent. Among the carbonate-based solvents, it is more preferable to mix a high dielectric constant carbonate-based organic solvent having a high ionic conductivity to be capable of increasing charge/discharge performance of the battery with a carbonate-based organic solvent having a low viscosity that is able to appropriately control the viscosity of the organic solvent having a high dielectric constant. Specifically, the organic solvent having a high dielectric constant selected from the group consisting of ethylene carbonate, propylene carbonate, and a mixture thereof, and the organic solvent having a low viscosity selected from the group consisting of ethylmethyl carbonate, dimethyl carbonate, diethyl carbonate, and a mixture thereof may be mixed to be used. More preferably, it is preferable to mix the organic solvent having a high dielectric constant and the organic solvent having a low viscosity at a volume ratio of 2:8 to 8:2. More specifically, ethylene carbonate or propylene carbonate; ethyl methyl carbonate; and dimethyl carbonate or diethyl carbonate may be mixed at a volume ratio of 5:1:1 to 2:5:3, preferably at a volume ratio of 3:5:2.

The lithium salt may be used without particular limitation as long as it is a compound capable of providing lithium ions used in the lithium secondary battery. Specifically, the lithium salt may be selected from the group consisting of $LiPF_6$, $LiClO_4$, $LiAsF_6$, $LiBF_4$, $LiSbF_6$, $LiAlO_4$, $LiAlCl_4$, $LiCF_3SO_3$, $LiC_4F_9SO_3$, $LiN(C_2F_5SO_3)$ $LiN(C_2F_5SO_2)_2$, $LiN(CF_3SO_2)_2$, $LiN(C_aF_{2a+1}SO_2)(C_bF_{2b+1}SO_2)$ (wherein a and b are natural numbers, preferably 1≤a≤20 and 1≤b≤20), LiCl, LiI, $LiB(C_2O_4)_2$ and a mixture thereof, and preferably lithium hexafluorophosphate ($LiPF_6$).

When the lithium salt is dissolved in the electrolyte, the lithium salt functions as a source of lithium ions in the lithium secondary battery and is able to promote movement of lithium ions between the cathode and the anode. Accordingly, it is preferable that the lithium salt has a concentration of about 0.6M to 2M in the electrolyte. When the concentration of the lithium salt is less than 0.6M, conductivity of the electrolyte may be lowered, and thus the performance of the electrolyte may be deteriorated. When the concentration thereof is more than 2M, viscosity of the electrolyte may be increased, and thus mobility of the lithium ion may be lowered. Considering the conductivity of the electrolyte and the mobility of lithium ions, it is more preferable that the concentration of the lithium salt is controlled to be approximately 0.7M to 1.6M in the electrolyte.

In addition to the above-described components of the electrolyte, the electrolyte may further include additives (hereinafter, referred to as other additives) that are generally usable for an electrolyte for the purpose of improving lifetime characteristic of the battery, suppressing reduction in battery capacity, and improving battery discharge capacity, etc.

Specific examples of the other additives may include vinylenecarbonate (VC), metal fluoride (for example, LiF, RbF, TiF, AgF, $AgF_2$, $BaF_2$, $CaF_2$, $CdF_2$, $FeF_2$, $HgF_2$, $Hg_2F_2$, $MnF_2$, $NiF_2$, $PbF_2$, $SnF_2$, $SrF_2$, $XeF_2$, $ZnF_2$, $AlF_3$, $BF_3$, $BiF_3$, $CeF_3$, $CrF_3$, $DyF_3$, $EuF_3$, $GaF_3$, $GdF_3$, $FeF_3$, $HoF_3$, $InF_3$, $LaF_3$, $LuF_3$, $MnF_3$, $NdF_3$, $PrF_3$, $SbF_3$, $ScF_3$, $SmF_3$, $TbF_3$, $TiF_3$, $TmF_3$, $YF_3$, $YbF_3$, $TlF_3$, $CeF_4$, $GeF_4$, $HfF_4$, $SiF_4$, $SnF_4$, $TiF_4$, $VF_4$, $ZrF_4$, $NbF_5$, $SbF_5$, $TaF_5$, $BiF_5$, $MoF_6$, $ReF_6$, $SF_6$, $WF_6$, $CoF_2$, $CoF_3$, $CrF_2$, CsF, $ErF_3$, $PF_3$, $PbF_3$, $PbF_4$, $ThF_4$, $TaF_5$, $SeF_6$, etc.), glutaronitrile (GN), succinonitrile (SN), adiponitrile (AN), 4-tolunitrile, 1,3,6-hexanetricarbonitrile, propylene sulfide (PS), 3,3'-thiodipropionitrile (TPN), vinylethylene carbonate (VEC), fluoroethylene carbonate (FEC), difluoroethylenecarbonate, fluorodimethylcarbonate, fluoroethylmethylcarbonate, lithium bis(trifluoromethylsulfonyl) imide (LiTFSI), lithium tetrafluoroborate ($LiBF_4$), lithium bis(oxalato)borate (LiBOB), lithium difluoro(oxalato)borate (LiDFOB), lithium (malonato oxalato) borate (LiMOB), lithium difluorophosphate ($LiPO_2F_2$) $LiPF_2C_4O_8$, $LiSO_3CF_3$, $LiPF_4$ $(C_2O_4)$ $LiP(C_2O_4)_3$, $LiC(SO_2CF_3)_3$, $LiBF_3$ $(CF_3CF_2)$ $LiPF_3$ $(CF_3CF_2)_3$, $Li_2B_{12}F_{12}$, 1,3-propane sultone, 1,3-propene sultone, biphenyl, cyclohexyl benzene, 4-fluorotoluene, succinic anhydride, ethylene sulfate anhydride, tris(trimethylsilyl)borate, etc., and these additives may be used alone or in combination of two or more thereof.

It is preferable that the other additives may have a content of 0.1 to 20 wt %, preferably 0.2 to 5 wt % based on the total weight of the electrolyte.

According to another exemplary embodiment of the present disclosure, there is provided a lithium secondary battery including the electrolyte. The lithium secondary battery according to an exemplary embodiment of the present disclosure may be classified into a lithium ion battery, a lithium ion polymer battery, and a lithium polymer battery depending on the type of the separator and the electrolyte used. The lithium secondary battery may be classified into a cylindrical type lithium secondary battery, a square type lithium secondary battery, a coin type lithium secondary battery, a pouch type lithium secondary battery, etc., depending on the shape, and may be divided into a bulk type lithium secondary battery and a thin film type lithium secondary battery depending on the size. Among these batteries, the electrolyte according to the exemplary embodiment of the present disclosure may be particularly excellent to be applied to a lithium ion battery, an aluminum laminated battery, and a lithium polymer battery.

Specifically, the lithium secondary battery includes a cathode and an anode that are disposed opposite to each other, wherein the cathode includes a cathode active material and the anode includes an anode active material, and the electrolyte interposed between the cathode and the anode.

FIG. 1 is a partial perspective view of a lithium secondary battery 1 according to an exemplary embodiment of the present disclosure. Referring to FIG. 1, the lithium secondary battery 1 according to another exemplary embodiment of the present disclosure may be produced by disposing an anode 3, a cathode 5, and a separator 7 interposed between the anode 3 and the cathode 5 to produce an electrode assembly 9, positioning the electrode assembly 9 in a case 15, and injecting a non-aqueous electrolyte thereinto so that the anode 3, the cathode 5, and the separator 7 are impregnated into the electrolyte.

Conductive lead members 10 and 13 for collecting a current generated at the time of battery operation may be attached to the anode 3 and the cathode 5, respectively, and the conductive lead members 10 and 13 may lead the currents generated in the cathode 5 and the anode 3 to cathode and anode terminals, respectively.

The cathode 5 may be produced by mixing a cathode active material, a conductive agent and a binder to prepare a composition for forming a cathode active material layer, and applying the composition for forming the cathode active material layer to a cathode current collector such as aluminum foil, or the like, followed by rolling.

As the cathode active material, a compound capable of performing reversible intercalation and deintercalation of lithium (a lithiated intercalation compound) may be used. Specifically, an olivine-type lithium metal compound represented by Chemical Formula 5 below may be used:

$$Li_xM_yM'_zXO_{4-w}Y_w \qquad \text{[Chemical Formula 5]}$$

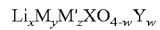

in Chemical Formula 5, M and M' are each independently an element selected from the group consisting of Fe, Ni, Co, Mn, Cr, Zr, Nb, Cu, V, Mo, Ti, Zn, Al, Ga, Mg, B, and a combination thereof, X is an element selected from the group consisting of P, As, Bi, Sb, Mo, and a combination thereof, Y is an element selected from the group consisting of F, S, and a combination thereof, 0<x≤1, 0<y≤1, 0<z≤1, 0<x+y+z≤2, and 0≤w≤0.5.

Among these compounds, in order to increase capacity characteristic and stability of the battery, it is preferable to select a material from the group consisting of $LiCoO_2$, $LiMnO_2$, $LiMn_2O_4$, $LiNiO_2$, $LiNi_xMn_{(1-x)}O_2$ (provided that $0<x<1$), $LiM_{1x}M_{2y}O_2$ (provided that $0≤x≤1$, $0≤y≤1$, $0≤x+y≤1$, $M_1$ and $M_2$ are each independently any one selected from the group consisting of Al, Sr, Mg and La), and a mixture thereof.

The anode 3 may be produced by mixing an anode active material, a binder and optionally a conductive agent in the same manner as the cathode 5 to prepare a composition for forming an anode active material layer, and then applying the composition to an anode current collector such as copper foil, etc.

As the anode active material, a compound capable of reversible intercalation and deintercalation of lithium may be used. Specific examples of the anode active material may include carbonaceous materials such as artificial graphite, natural graphite, graphitized carbon fiber, and amorphous carbon, etc. Further, in addition to the carbonaceous material, a metallic compound capable of being alloyed with lithium, or a composite material including the metallic compound and the carbonaceous material may be used as the anode active material.

At least one of Si, Al, Sn, Pb, Zn, Bi, In, Mg, Ga, Cd, Si alloy, Sn alloy and Al alloy may be used as the metal capable of being alloyed with lithium. In addition, a metal lithium thin film may be used as the anode active material.

As the anode active material, any one selected from the group consisting of crystalline carbon, amorphous carbon, carbon composite, lithium metal, alloy including lithium, and a mixture thereof may be used in view of high stability.

Meanwhile, since the electrolyte is the same as described above in connection with the electrolyte, description thereof will be omitted. The lithium secondary battery may be produced by a conventional method, and thus, detailed description thereof will be omitted herein. Even though the pouch type lithium secondary battery is described as an example in the present exemplary embodiment, the present disclosure is not limited to the pouch type lithium secondary battery, and may have any shape as long as it is operable as a battery.

As described above, the lithium secondary battery including the electrolyte according to the exemplary embodiment of the present disclosure may exhibit low DC-IR characteristic, high-temperature storage characteristic, and improved output characteristic to thereby be useful for portable devices such as a mobile phone, a notebook computer, a digital camera, and a camcorder, etc., that require a fast charging speed, electric vehicles such as hybrid electric vehicle (HEV), plug-in hybrid electric vehicles (PHEV), etc., and medium and large energy storage systems.

DETAILED DESCRIPTION OF THE DISCLOSURE

Hereinafter, exemplary embodiments of the present disclosure will be described in detail with reference to the accompanying drawings so that they can be easily carried out by those skilled in the art. However, the present disclosure may be modified in various different ways and is not limited to the exemplary embodiments provided in the present description.

Preparation Example: Preparation of Electrolytic Solution and Production of Lithium Secondary Battery As a cathode, slurry prepared by mixing $LiCoO_2$ as a cathode active material, carbon black as a conductive agent, polyvinylidene fluoride (PVDF) as a binder, and n-methyl-2-pyrrolidone (NMP) as a solvent was coated on an aluminum (Al) substrate to be used. In addition, as an anode, slurry prepared by mixing mesocarbon microbead (MCMB) which was artificial graphite and carbon black, PVDF as a binder, and NMP as a solvent was coated on a copper (Cu) substrate to be used.

Example 1

$LiPF_6$ (1.15M) was added to a solution in which ethylene carbonate (EC), ethylmethyl carbonate (EMC), and dimethyl carbonate (DEC) are mixed with each other (volume ratio: EC/EMC/DEC=3/5/2), and then 1 wt % of perfluoropentanenitrile as an electrolytic solution additive was added based on the total weight of the obtained mixed solution, thereby preparing an electrolytic solution. An aluminum pouch type (Al-pouch type) lithium secondary battery was produced by using the electrolytic solution prepared above and cathode and the anode previously produced.

Example 2

$LiPF_6$ (1.15M) was added to a solution in which ethylene carbonate (EC), ethylmethyl carbonate (EMC), and dimethyl carbonate (DEC) are mixed with each other (volume ratio: EC/EMC/DEC=3/5/2), and then 1 wt % of perfluorohexane-1,6-dinitrile as an electrolytic solution additive was added based on the total weight of the obtained mixed solution, thereby preparing an electrolytic solution. An aluminum pouch type (Al-pouch type) lithium secondary battery was produced by using the electrolytic solution prepared above and cathode and anode previously produced.

Example 3

$LiPF_6$ (1.15M) was added to a solution in which ethylene carbonate (EC), ethylmethyl carbonate (EMC), and dimethyl carbonate (DEC) are mixed with each other (volume ratio: EC/EMC/DEC=3/5/2), and then 1 wt % of 3-(cyanodifluoromethyl)-2,2,3,4,4-pentafluoropentanedinitrile as an electrolytic solution additive was added based on the total weight of the obtained mixed solution, thereby preparing an electrolytic solution. An aluminum pouch type (Al-pouch type) lithium secondary battery was produced by using the electrolytic solution prepared above and cathode and anode previously produced.

Example 4

$LiPF_6$ (1.15M) was added to a solution in which ethylene carbonate (EC), ethylmethyl carbonate (EMC), and dimethyl carbonate (DEC) are mixed with each other (volume ratio: EC/EMC/DEC=3/5/2), and then 1 wt % of 3,3-bis(cyanodifluoromethyl)-2,2,4,4-tetrafluoropentanedinitrile as an electrolytic solution additive was added based on the total weight of the obtained mixed solution, thereby preparing an electrolytic solution. An aluminum pouch type (Al-pouch type) lithium secondary battery was produced by using the electrolytic solution prepared above and cathode and anode previously produced.

Example 5

$LiPF_6$ (1.15M) was added to a solution in which ethylene carbonate (EC), ethylmethyl carbonate (EMC), and dimethyl carbonate (DEC) are mixed with each other (volume ratio: EC/EMC/DEC=3/5/2), and then 0.8 wt % of perfluorohexane-1,6-dinitrile and 0.2 wt % of hexane-1,6-dinitrile as electrolytic solution additives were added based on the total weight of the obtained mixed solution, thereby preparing an electrolytic solution. An aluminum pouch type (Al-pouch type) lithium secondary battery was produced by using the electrolytic solution prepared above and cathode and anode previously produced.

Comparative Example 1

$LiPF_6$ (1.15M) was added to a solution in which ethylene carbonate (EC), ethylmethyl carbonate (EMC), and dimethyl carbonate (DEC) are mixed with each other (volume ratio: EC/EMC/DEC=3/5/2), and then 1 wt % of a compound in which only a part in Chemical Formula 1 is substituted with fluorine as an electrolytic solution additive was added based on the total weight of the obtained mixed solution, thereby preparing an electrolytic solution. An aluminum pouch type lithium secondary battery was produced by using the electrolytic solution prepared above and cathode and anode previously produced.

Comparative Example 2

$LiPF_6$ (1.15M) was added to a solution in which ethylene carbonate (EC), ethylmethyl carbonate (EMC), and dimethyl carbonate (DEC) are mixed with each other (volume ratio: EC/EMC/DEC=3/5/2), and then 1 wt % of a compound in which only a part in Chemical Formula 2 is substituted with fluorine as an electrolytic solution additive was added based on the total weight of the obtained mixed solution, thereby preparing an electrolytic solution. An aluminum pouch type (Al-pouch type) lithium secondary battery was produced by using the electrolytic solution prepared above and the cathode and the anode previously produced.

Comparative Example 3

$LiPF_6$ (1.15M) was added to a solution in which ethylene carbonate (EC), ethylmethyl carbonate (EMC), and dimethyl carbonate (DEC) are mixed with each other (volume ratio: EC/EMC/DEC=3/5/2), and then 1 wt % of a compound in which only a part in Chemical Formula 3 is substituted with fluorine as an electrolytic solution additive was added based on the total weight of the obtained mixed solution, thereby preparing an electrolytic solution. An aluminum pouch type (Al-pouch type) lithium secondary battery was produced by using the electrolytic solution prepared above and the cathode and the anode previously produced.

Comparative Example 4

$LiPF_6$ (1.15M) was added to a solution in which ethylene carbonate (EC), ethylmethyl carbonate (EMC), and dimethyl carbonate (DEC) are mixed with each other (volume ratio: EC/EMC/DEC=3/5/2), and then 1 wt % of a compound in which only a part in Chemical Formula 4 is substituted with fluorine as an electrolytic solution additive was added based on the total weight of the obtained mixed solution, thereby preparing an electrolytic solution. An aluminum pouch type (Al-pouch type) lithium secondary battery was produced by using the electrolytic solution prepared above and the cathode and the anode previously produced.

Comparative Example 5

$LiPF_6$ (1.15M) was added to a solution in which ethylene carbonate (EC), ethylmethyl carbonate (EMC), and dimethyl carbonate (DEC) are mixed with each other (volume ratio: EC/EMC/DEC=3/5/2), and then 1 wt % of hexane-1,6-dinitrile as an electrolytic solution additive was added based on the total weight of the obtained mixed solution, thereby preparing an electrolytic solution. An aluminum pouch type (Al-pouch type) lithium secondary battery was produced by using the electrolytic solution prepared above and the cathode and the anode previously produced.

Experimental Example 1: Capacity Evaluation of Lithium Secondary Battery

Batteries produced in Comparative Examples 1 to 5 and Examples 1 to 5 were charged at 1.0 C-CCCV-4.45V, and 0.04 C, respectively, and after resting for 10 minutes, the batteries were discharged up to 1.0 C-CC-3.0V and rested for 10 minutes. The efficiency was measured while repeating the cycle 300 times and shown in Table 1. Further, data of Example 2, Comparative Example 2, and Comparative Example 5 were shown in FIG. 2.

TABLE 1

| Composition of electrolytic solution | Discharge capacity after 1 cycle (mAh) | Discharge capacity after 200 cycles (mAh) | Efficiency (%) |
|---|---|---|---|
| Comparative Example 1 (only a part in Chemical Formula 1 is substituted with fluorine) | 840.7 | 336 | 40.1 |
| Comparative Example 2 (only a part in Chemical Formula 2 is substituted with fluorine) | 841.1 | 339.4 | 40.4 |
| Comparative Example 3 (only a part in Chemical Formula 3 is substituted with fluorine) | 840.8 | 339.6 | 40.4 |
| Comparative Example 4 (only a part in Chemical Formula 4 is substituted with fluorine) | 840.1 | 338.6 | 40.3 |
| Comparative Example 5 (hexane-1, 6-dinitrile) | 841.1 | 339.4 | 40.4 |
| Example 1 (Chemical Formula 1) | 841.3 | 696.6 | 82.8 |
| Example 2 (Chemical Formula 2) | 840.9 | 697.2 | 83.1 |
| Example 3 (Chemical Formula 3) | 840.8 | 696.2 | 82.8 |
| Example 4 (Chemical Formula 4) | 841.2 | 696.1 | 83.0 |
| Example 5 (Chemical Formula 2 + hexane-1,6-dinitrile) | 841.3 | 696.6 | 82.8 |

Figure 2:
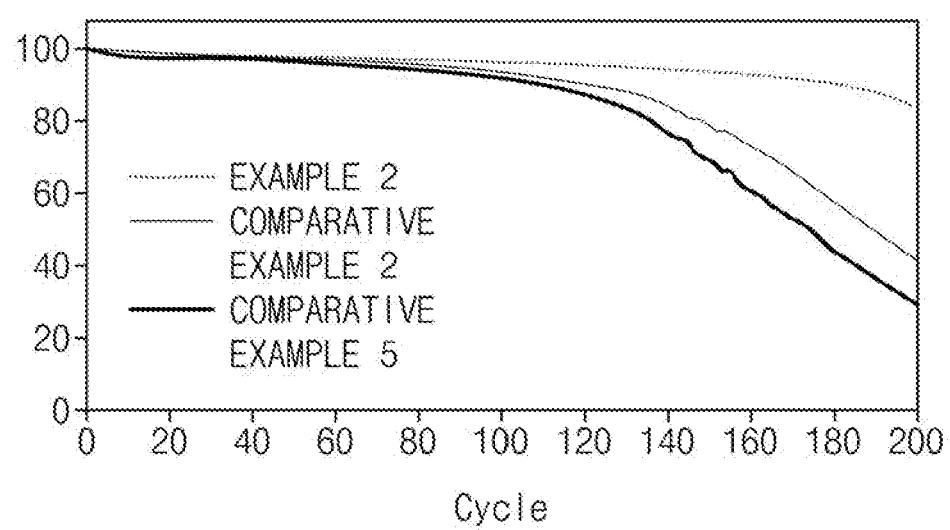
FIG. 2 is a graph showing lifetime characteristics of lithium secondary batteries according to Examples and Comparative Examples of the present disclosure.

Referring to Table 1 and FIG. 2, when the battery was charged/discharged at a high voltage, the efficiency of Comparative Example was reduced by half or more, but the efficiency of Example using the electrolyte according to the present disclosure was twice as high as that of Comparative Example.

As a result, it could be confirmed that according to the present disclosure, the battery characteristics of the lithium secondary battery, particularly, the cathode film forming characteristic and the battery resistance characteristic at a high voltage could be improved.

Experimental Example 2: Storage Evaluation of Lithium Secondary Battery

The batteries produced in Example 2, Example 5, and Comparative Example 2 were charged at 4.45 V and stored for 4 weeks at 60□, wherein a remaining discharge solution of the battery was measured to measure a recovery capacity, and whether swelling of the battery occurred was measured to determine swelling characteristic. Results thereof were shown in Tables 2 and 3, respectively.

TABLE 2

|  | Comparative Example 5 (mAh) | Example 2 (mAh) | Example 5 (mAh) |
| --- | --- | --- | --- |
| $1^{st}$ week | 691.3 | 692.7 | 697.1 |
| $2^{nd}$ week | 671.8 | 682.1 | 694.2 |
| $3^{rd}$ week | 664.2 | 665.3 | 688.4 |
| $4^{th}$ week | 1631.2 | 1653.9 | 674.5 |

TABLE 3

|  | Comparative Example 5 (mm) | Example 2 (mm) | Example 5 (mm) |
| --- | --- | --- | --- |
| $1^{st}$ week | 2.84 | 2.84 | 2.65 |
| $2^{nd}$ week | 2.86 | 2.74 | 2.66 |
| $3^{rd}$ week | 3.98 | 3.64 | 2.71 |
| $4^{th}$ week | 3.99 | 3.68 | 2.72 |

Referring to Tables 2 and 3, it could be confirmed that even though the hexane-1,6-dinitrile used in Comparative Example 5 had a poor recovery capacity and a poor swelling characteristic as compared to the perfluorohexane-1,6-dinitrile used in Example 2, Example 5 where the hexane-1,6-dinitrile and the perfluorohexane-1,6-dinitrile were mixed together obtained a synergistic effect in which the recovery capacity and the swelling characteristic were further improved even though the total content of the electrolytic solution additive was the same as compared to Example 2 using only the perfluorohexane-1,6-dinitrile.

While the present disclosure has been described with reference to preferable exemplary embodiments of the present disclosure, it is to be understood that the present disclosure is not limited to the disclosed embodiments, but, on the contrary, is intended to cover various modifications and equivalent arrangements included within the spirit and scope of the appended claims.

DETAILED DESCRIPTION OF MAIN ELEMENTS

1: Lithium secondary battery
3: Anode
5: Cathode
7: Separator
9: Electrode assembly
10, 13: Lead member
15: Case

INDUSTRIAL APPLICABILITY

The present disclosure relates to an electrolyte for a lithium secondary battery and a lithium secondary battery including the same, wherein the electrolyte for a lithium secondary battery may improve the battery characteristics of the lithium secondary battery, particularly, the cathode film forming characteristic and the battery resistance characteristic at the high voltage.

The invention claimed is:

1. An electrolyte for a lithium secondary battery comprising:
a perfluoro nitrile compound as an electrolyte additive,
wherein the perfluoro nitrile compound is selected from the group consisting of a perfluoro dinitrile compound, a perfluoro trinitrile compound, a perfluoro tetranitrile compound, and a combination thereof.

2. The electrolyte for a lithium secondary battery according to claim 1, wherein the perfluoro nitrile compound is perfluorohexane-1,6-dinitrile.

3. The electrolyte for a lithium secondary battery according to claim 2, further comprising hexane-1,6-dinitrile.

4. The electrolyte for a lithium secondary battery according to claim 3, wherein the hexane-1,6-dinitrile has a content of 1 to 80 parts by weight based on 100 parts by weight of the perfluorohexane-1,6-dinitrile.

5. The electrolyte for a lithium secondary battery according to claim 1, further comprising an organic solvent and a lithium salt.

6. The electrolyte for a lithium secondary battery according to claim 1, wherein the perfluoro nitrile compound is represented by Chemical Formulas 1 to 3 below:

[Chemical Formula 1]
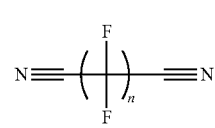

[Chemical Formula 2]
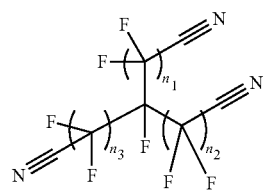

[Chemical Formula 3]
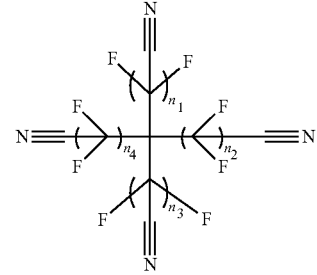

wherein n is 1 to 15.

7. A lithium secondary battery comprising:
a cathode including a cathode active material, an anode disposed opposite to the cathode and including an anode active material, and
an electrolyte interposed between the cathode and the anode, wherein the electrolyte includes a perfluoro nitrile compound as an electrolyte additive,
wherein the perfluoro nitrile compound is selected from the group consisting of a perfluoro dinitrile compound, a perfluoro trinitrile compound, a perfluoro tetranitrile compound, and a combination thereof.

8. The lithium secondary battery according to claim 7, wherein the electrolyte additive has a content of 0.1 to 10 wt % based on the total weight of the electrolyte.

9. The lithium secondary battery according to claim 7, wherein the perfluoro nitrile compound is perfluorohexane-1,6-dinitrile.

10. The lithium secondary battery according to claim 9, wherein the electrolyte for a lithium secondary battery further includes hexane-1,6-dinitrile.

11. The lithium secondary battery according to claim 10, wherein the hexane-1,6-dinitrile has a content of 1 to 80 parts by weight based on 100 parts by weight of the perfluorohexane-1,6-dinitrile.

12. The lithium secondary battery according to claim 7, wherein the perfluoro nitrile compound is represented by Chemical Formulas 1 to 3 below:

[Chemical Formula 1]

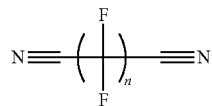

[Chemical Formula 2]

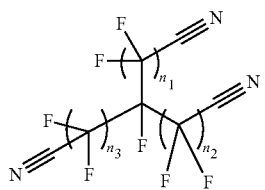

[Chemical Formula 3]

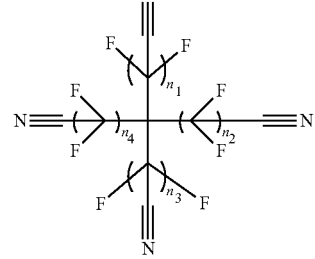

wherein n is 1 to 15.

* * * * *